United States Patent [19]

Stealey et al.

[11] Patent Number: 4,988,707

[45] Date of Patent: Jan. 29, 1991

[54] PHARMACOLOGICALLY ACTIVE PHENYLALKANOYL SUBSTITUTED IMIDAZO (4,5-C) PYRIDINES

[75] Inventors: Michael A. Stealey, Libertyville; Richard M. Weier, Lake Bluff, both of Ill.

[73] Assignee: G. D. Searle & Co., Chicago, Ill.

[21] Appl. No.: 406,638

[22] Filed: Sep. 13, 1989

[51] Int. Cl.$^5$ .................. A61K 31/44; C07D 471/04
[52] U.S. Cl. ........................................ 514/303; 546/118
[58] Field of Search ...................... 546/118; 514/303

[56] References Cited

U.S. PATENT DOCUMENTS

| | | | |
|---|---|---|---|
| 4,327,100 | 4/1982 | Austel et al. | 546/118 |
| 4,336,257 | 6/1982 | Baldwin | 546/118 |
| 4,716,160 | 12/1981 | Markwell et al. | 546/119 |
| 4,804,658 | 2/1989 | Manley et al. | 546/118 |

FOREIGN PATENT DOCUMENTS

| | | |
|---|---|---|
| 83302433.4 | 11/1983 | European Pat. Off. |
| 87113294.0 | 3/1988 | European Pat. Off. |
| 87114979.5 | 4/1988 | European Pat. Off. |
| 871148417 | 5/1988 | European Pat. Off. |

Primary Examiner—Mary C. Lee
Assistant Examiner—Bernard I. Dentz
Attorney, Agent, or Firm—Joy Ann Serauskas; Paul D. Matukaitis

[57] ABSTRACT

This invention relates to substituted imidazopyridine dervatives having the following formula $$\text{structure I: imidazo[4,5-c]pyridine with } R_3, R_4 \text{ substituents and } N_5-(CH_2)_n-Y-\overset{O}{\underset{\|}{C}}-(CH_2)_m-CH\overset{R_1}{\underset{R_2}{}}$$

and isomers thereof;

or a pharmaceutically acceptable acid addition salt thereof: wherein $R_1$ and $R_2$ are each independently selected from hydrogen; straight or branched chain alkyl of 1 to 15 carbon atoms; cycloalkyl of 3 to 8 carbon atoms; cycloalkyl which can be substituted once or more by alkyl of 1 to 6 carbon atoms; phenyl; phenyl which can be substituted once or more by alkyl of 1 to 6 carbon atoms or halogen; straight or branched alkenyl having 3 to 15 carbon atoms.

y is phenyl or phenyl substituted once or more by alkyl of 1 to 6 carbon atoms; alkoxy wherein the alkyl is 1 to 6 carbon atoms; and halogen selected from the group consisting of bromo, fluoro or chloro.

m is an integer from 0 to 5.

n is an integer from 1 to 5.

$R_3$ is a group substituted at one or more of the 4, 6 or 7 positions of the pyridine ring said groups being independently selected from hydrogen, alkyl of 1 to 6 carbon atoms; halogen wherein the halogen is selected from bromo, fluoro, or chloro; or alkoxy wherein the alkyl is 1 to 6 carbon atoms;

$R_4$ is hydrogen or alkyl of 1 to 4 carbon atoms.

useful in the treatment of diseases or disorders mediated by platelet-activating factor. This invention also relates to pharmaceutical compositions of such substituted imidazopyridines.

16 Claims, No Drawings

PHARMACOLOGICALLY ACTIVE PHENYLALKANOYL SUBSTITUTED IMIDAZO (4,5-C) PYRIDINES

FIELD OF THE INVENTION

This invention is in the field of mammalian therapeutics and relates to compounds for treatment of mammalian diseases such as inflammation, cardiovascular disorders, asthma and other diseases. Of particular interest is a class of Phenylalkanoyl Substituted Imidazo [4,5-c] Pyridines useful for treatment of cardiovascular and immuno-inflammatory related disorders mediated by platelet activating factor (PAF).

BACKGROUND OF THE INVENTION

Platelet-activating factor (PAF) has been associated with various biological activities and pathways, thus making it an important mediator responsible for a variety of physiological processes including, but not limited to, activation and aggregation of platelets, smooth muscle contraction, pathogenesis of immune complex deposition, inflammation, and respiratory, cardiovascular and intravascular alterations. These physiological processes are associated with a large group of diseases, such as, for example, cardiovascular disorders, asthma, lung edema, endotoxin shock, adult respiratory distress syndrome and inflammatory diseases.

U.S. Pat. No. 4,804,658 discloses a class of imidazopyridine derivatives useful in the treatment of diseases or disorders mediated by platelet-activating factor. The present invention is distinct from this disclosure in that in the present invention a phenylalkanoyl is attached to the nitrogen (position 5) which makes up the six membered ring of the imidazopyridine ring system as opposed to the disclosure wherein a benzamide moiety is attached to one of the nitrogens which makes up the five membered ring of the imidazopyridine ring system.

SUMMARY OF THE INVENTION

The present invention relates to a novel class of compounds represented by the formula

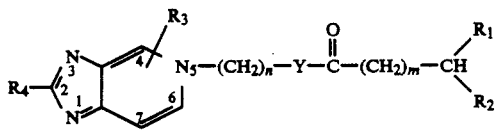

I $R_1$ and $R_2$ are each independently selected from hydrogen; straight or branched chain alkyl of 1 to 15 carbon atoms; cycloalkyl of 3 to 8 carbon atoms; cycloalkyl which can be substituted once or more by alkyl of 1 to 6 carbon atoms; phenyl; phenyl which can be substituted once or more by alkyl of 1 to 6 carbon atoms or halogen; straight or branched alkenyl having 3 to 15 carbon atoms.

y is phenyl or phenyl substituted once or more by alkyl of 1 to 6 carbon atoms; alkoxy wherein the alkyl is 1 to 6 carbon atoms; and halogen selected from the group consisting of bromo, fluoro or chloro.

m is an integer from 0 to 5.

n is an integer from 1 to 5.

$R_3$ is a group substituted at one or more of the 4, 6 or 7 positions of the pyridine ring said groups being independently selected from hydrogen, alkyl of 1 to 6 carbon atoms; halogen wherein the halogen is selected from bromo, fluoro, or chloro; or alkoxy wherein the alkyl is 1 to 6 carbon atoms.

$R_4$ is hydrogen or alkyl of 1 to 4 carbon atoms.

The invention further relates to pharmaceutical compositions comprising a compound of formula I. Such compounds and compositions have potent and specific PAF antagonistic activities and are thereby useful in the treatment of various diseases or disorders mediated by the PAF, for example inflammation, cardiovascular disorders, asthma, lung edema, and adult respiratory distress syndrome.

A preferred embodiment of the present invention are compounds of the formula

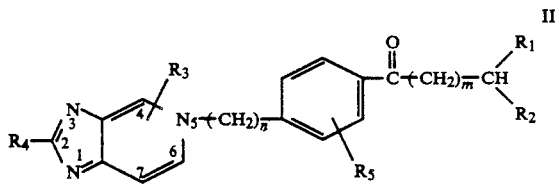

II or a pharmaceutically acceptable acid addition salt thereof; wherein $R_1$ and $R_2$ are each independently selected from hydrogen; straight o branched chain alkyl of 1 to 15 carbon atoms; cycloalkyl of 3 to 8 carbon atoms; substituted cycloalkyl wherein the substituent is alkyl of 1 to 6 carbon atoms; straight or branched alkenyl having 3 to 15 carbon atoms;

m is an integer from 0 to 5 n is an integer from 1 to 5

$R_3$ is hydrogen or alkyl of 1 to 6 carbon atoms $R_4$ is hydrogen or alkyl of 1 to 4 carbon atoms $R_5$ is selected from hydrogen; alkyl of 1 to 6 carbon atoms; alkoxy wherein the alkyl is 1 to 6 carbon atoms; and halogen selected from the group consisting of bromo, fluoro or chloro.

As used herein the term "alkyl of 1 to 15 carbon atoms": refers to straight chain or branched chain hydrocarbon groups having from one to fifteen carbon atoms. Illustrative of such alkyl groups are methyl, ethyl, propyl isopropyl, butyl, isobutyl, pentyl, neopentyl, hexyl, isohexyl, octyl, decyl and the like.

As used herein the term "cycloalkyl of 3 to 8 carbon atoms" included cycloalkyl groups having from three to eight carbons. Illustrative of such cycloalkyl groups are cyclopropyl, cyclobutyl, cyclopentyl, cyclohexyl, cycloheptyl, cyclooctyl and the like.

As used herein the term halogen includes fluoro, chloro and bromo.

As used herein the term "alkenyl having 2 to 15 carbon atoms" refers to straight or branched unsaturated hydrocarbon groups having from 2 to 15 carbon atoms. Illustrative of such alkenyl groups are 2-propenyl, hexenyl, octenyl, decenyl and the like.

As used herein the term "alkoxy" wherein the alkyl is 1 to 6 carbon atoms refers to straight or branched chain ethers. Illustrative of such groups are methoxy, ethoxy, propoxy, butoxy, isopropoxy and the like.

Included within the embodiments of the present invention are the tautomeric forms of the described compounds, isomeric forms including geometric isomers, enantiomers and diastereoisomers, and the pharmaceutically acceptable salts thereof.

The term "pharmaceutically acceptable acid addition salt" refers to a salt prepared by contacting a compound of formula (I) with an acid whose union is generally considered suitable for human consumption. Examples of pharmacologically acceptable acid addition salts include but are not limited to the hydrochloride, hydrobromide, hydroiodide, sulfate, phosphate, acetate, propionate, lactate, maleate, malate, succinate, and tartrate salts. All of these sakts nat be prepared by conventional means by reacting, for example, the appropriate acid with the corresponding compound of Formula I.

The compounds of formula I may be prepared in accordance with the following procedures.

yaluminum hydride. The alcohol 5 is converted to the chloride 6 by reaction with halogenating reagents such as thionyl chloride. Chloride 6 is converted to the target compound 8 by reaction with imidazopyridine 7 in a solvent such as dimethyl acetamide at temperatures ranging up to 115°.

Alternatively, when $R_1=H$ and $R_2=$cycloalkyl, compound 3 can be alkylated with halides such as allyl iodide using a strong base such as t-BuOK in dimethylformamide at room temperature to 50°. This yields 3 ($R_1=$allyl, $R_2=$cycloalkyl). Compound 3 is then converted to 8 as described above.

A second approach to the synthesis of ketones of this

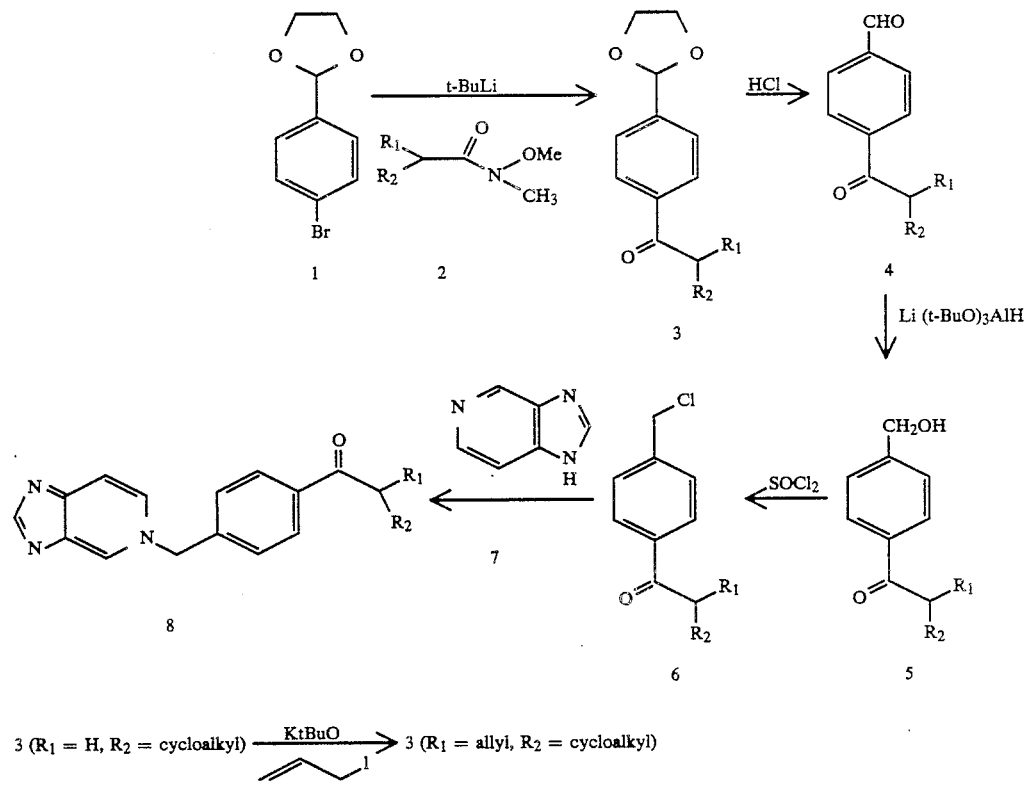

Scheme A $R_1$ and $R_2$ are defined as before.

The ethylene acetal of p-bromobenzaldehyde (1) of Scheme A can be lithiated at low temperature (−78° to −40°) with reagents such a t butyl lithium. The lithiated intermediate can be condensed with appropriately substituted N-methoxy-N-methyl acetic acid amides (2) at temperatures ranging from −78° to 0° to give ketones such as 3 as products. Removal of the ethylene acetal is effected by acid hydrolysis and selective reduction of the revealed aldehyde carbonyl to the benzyl alcohol 5 is carried out using reagents such as lithium tri-t-butoxstructure is to use as starting material the corresponding protected benzaldehyde bearing a carboxyl on the aromatic ring. This is converted to the N,O-dimethyl hydroxylamide using chemistry similar to that described above. This amide is converted to the ketone by reaction with a suitable organometallic reagent bearing the desired alkyl substituent. Utilizing chemistry similar to that described above, the masked aldehyde is converted to the chloromethyl derivative and this coupled with the starting imidazopyridine to give the target compound.

Scheme B

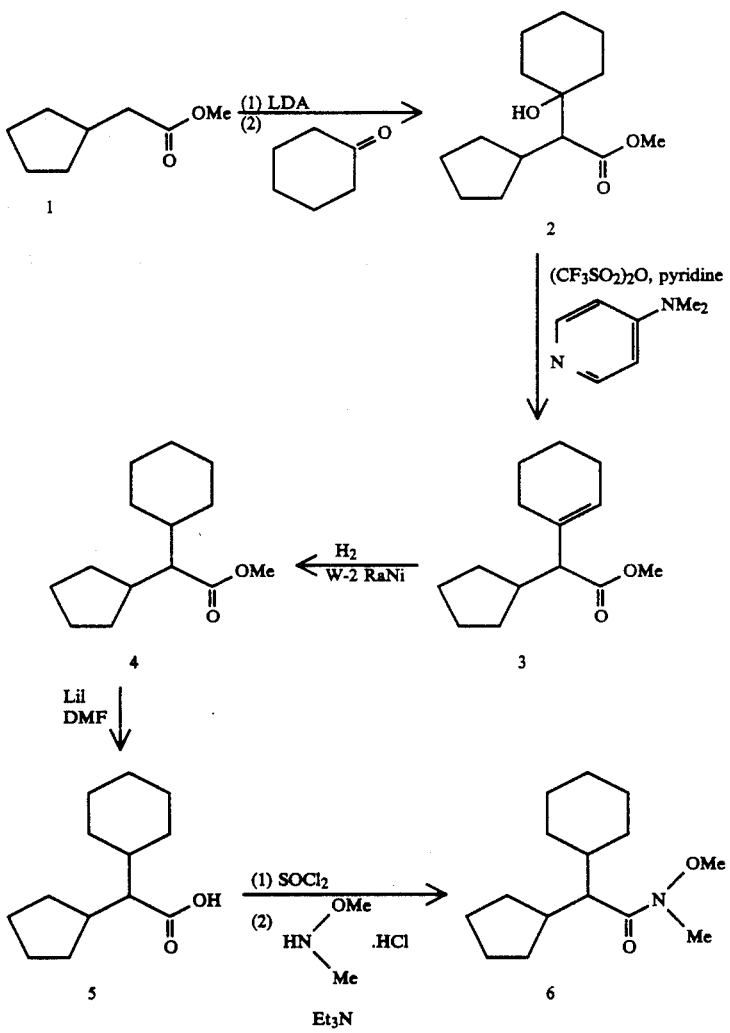

R₁ and R₂ are defined as before

Disubstituted amides 2 (e.g., R₁ and R₂=cycloalkyl) of Scheme A may be synthesized from the corresponding monosubstituted intermediates as exemplified in Scheme B. Thus, methyl cyclopentaneacetate 1 is converted to hydroxyester 2 by condensation of its enolate with cyclohexanone at low temperature (−70°). Ester 2 is dehydrated to 3 by reaction with trifluoromethanesulfonic acid anydride in pyridine containing 4-dimethylamino pyridine with warming to 50°. Olefin 3 is reduced to 4 by hydrogenation using W-2 Raney Nickel as catalyst. Compound 4 is converted to acid 5 by treatment with excess lithium iodide in DMF at reflux. Acid 5 is converted to amide 6 by reaction first with thionyl chloride, and then reaction of the resultant acid chloride with N, O-dimethyl hydroxylamine hydrochloride in dichloroethane containing triethylamine at temperatures ranging from room temperature to 50°.

The compounds of formula II wherein R₅ is alkoxy can be prepared by beginning with 2-methoxy-4-bromobenzaldehyde which can be prepared according to the procedure described by Armstrong et al. Synthetic Communications 18 717 (1988) or Glennon, et al. J. Med. Chem. 29 194 (1986) and then following the procedures which are described in Examples C to G.

This invention also relates to a method of treatment for patients (or mammalian animals raised in the dairy, meat, or fur industries or as pets) suffering from disorders or diseases which can be attributed to PAF as previously described, and more specifically, a method of treatment involving the administration of compound (I) as the active ingredient.

Accordingly, compound (I) can be used among other things to reduce inflammation, to correct respiratory, cardiovascular, and intravascular alterations or disorders, and to regulate the activation or coagulation of platelets, the pathogenesis of immune complex deposition and smooth muscle contractions.

For the treatment of inflammation, cardiovascular disorder, asthma, or other diseases mediated by PAF, compound (I) may be administered orally, topically, parenterally, or by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients. The compounds and composition may for example be administered intravascularly, orally, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit contained in a particular amount of the active ingredient. Examples of such dosage units are tablets or capsules. These may with advantage contain an amount of active ingredient from about 1 to 250 mg preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight.

The dosage regimen for treating an infectious disease condition with the compounds and/or compositions of this invention is selected in accordance with a variety of factors, including the type, age, weight, sex and medical condition of the patient; the severity of the infection; the route of administration; and the particular compound employed and thus may vary widely.

For therapeutic purposes, the compounds of this invention are ordinarily combined with one or more adjuvants appropriate to the indicated route of administration. If per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and thus tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art. Appropriate dosages, in any given instance, of course depend upon the nature and severity of the condition treated, the route of administration, and the species of mammal involved, including its size and any individual idiosyncrasies.

Representative carriers, diluents and adjuvants include for example, water, lactose, gelatin, starches, magnesium stearate, talc, vegetable oils, gums, polyalkylene glycols, petroleum jelly, etc. The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

Dosage levels of the order from about 0.1 mg to about 1000 mg per kilogram of body weight per day are useful in the treatment of the above-indicated conditions (from about 50 mg to about 5 mgs. per patient per day). For example, inflammation is effectively treated and anti-pyretic and analgesic activity manifested by the administration from about 25 to about 75 mg of the compound per kilogram of body weight per day (about 75 mg to about 3.75 gm per patient per day). Preferably, from about 5 mg to about 50 mg per kilogram of body weight per daily dosage produces highly effective results (about 250 mg to about 2.5 gm per patient per day).

The amount of active ingredient that may be combined with the carrier materials to produce a single dosage form will vary depending upon the host treated and the particular mode of administration. For example, a formulation intended for the oral administration of humans may contain from 5 mg to 95 mg of active agent compounded with an appropriate and convenient amount of carrier material which may vary from about 5 to 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Examples are intended to further illustrate the present invention and not to limit the invention in spirit or scope. In the Examples, all parts are parts by weight unless otherwise expressly set forth.

PREPARATION OF STARTING MATERIALS

EXAMPLE A

Preparation of Cyclopentanacetyl Chloride

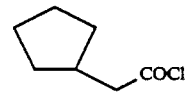

Cyclopentane acetic acid (17 g, 0.132mole) was stirred into 50 mls of thionyl chloride and refluxed for two hours. The mixture was cooled and the excess solvent was removed via distillation at atmospheric pressure. The residue was distilled (b.p.=38°-39° C. at 0.1 mm Hg) to give 15 g of the title compound (81% distilled yield).

EXAMPLE B

Preparation of N-Methoxy-N-Methyl Cyclopentaneacetamide

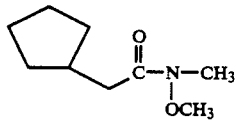

N,O-Dimethylhydroxylamine hydrochloride (13 g, 0.12mole) was stirred in 250 mls of dichloroethane and cooled to 0° C. under argon. Triethylanime (25 g, 0.25mole) was added dropwise over 15 minutes and the mixture stirred cold for 30 minutes. The acid chloride of Example A (15 g,0.1mole) was dissolved in dichloroethane (50 mls) and added at 0° C. over ½ hour to the mixture. The mixture was then stirred for an additional hour at 0° C. The mixture was allowed to warm to room temperature over 2 hours and the solvent was removed in vacuo. The residue was treated with 100 mls of ethyl acetate/ether (25:75) and the triethylamine hydrochloride filtered. The filtrate was stripped of solvent and the residue distilled at 0.1 mm Hg, b.p.=62°-63° C. to give 12 g (70% yield) of the title compound.

EXAMPLE C

Preparation of 2-(4-Bromophenyl) Dioxolane

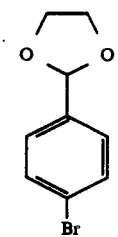

4-Bromobenzaldehyde (56 g, 0.3 mole) was dissolved in 500 mls of benzene containing 80 mls (excess) of ethylene glycol. This mixture was stirred rapidly via motor. p-Toluenesulfonic acid (5 g) was added and the mixture was refluxed with a water separator overnight (24 hours). The cooled mixture was poured into 1 liter of 5% $K_2CO_3$ and extracted with ethyl acetate. The organic phase was washed with $H_2O$ and then brine. The extract was dried over sodium sulfate and filtered. After solvent removal, the residue was chromatographed on silica gel using 10% ethyl acetate/hexane to give 50 g (70% yield.) of the title compound (m.p.=56°-57° C.).

EXAMPLE D

Preparation of 2-Cyclopentyl-1-[4-(2-Dioxolanyl)Phenyl]Ethanone

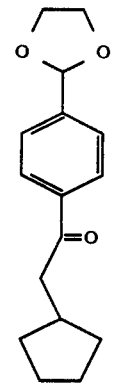

2-(4-Bromophenyl)dioxolane from Example C (7 g, 0.03 mole) was dissolved in 75 mls of THF and cooled to -75° C. under argon. Tert.butyl lithium (29 ml of 1.7M solution in hexane) was added slowly at -76° C. maintaining the temperature such that it never rose above -40° C. After addition was complete, the solution was recooled to -78° C. and 4.2 g, 0.024 moles) of the product of Example B was added in THF. After completion of the addition, the solution was allowed to warm to 0° C., poured into 0.5N $KHSO_4$ and extracted with ethyl acetate. After washing with brine, the extract was dried over $Na_2SO_4$. After the solvent was removed, the residue was chromatographed on silica with 10% ethyl acetate/hexane to give 2.8 g of the title compound.

EXAMPLE E

Preparation of 4-(2-Cyclopentyl-1-Oxoethyl)Benzenecarboxaldehyde

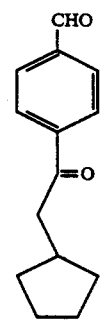

The product of Example D (2.8 g, 0.011 mole) was dissolved in 50 mls of THF and 5 mls of 1N HCl was added. The mixture was refluxed for 3 hours and cooled. The solvent was removed on the rotary evaporator. The residue was dissolved in ethyl acetate and washed with 7% $NaHCO_3$. After drying the solution over $Na_2SO_4$, the organic layer was concentrated on the rotary evaporator and the residue was chromatographed on silica gel using 5% ethyl acetate/hexane to give 2.2 g of the title compound (95% yield) as an oil.

EXAMPLE F

Preparation of 2-Cyclopentyl-1-[4-(Hydroxymethyl)Phenyl]Ethanone

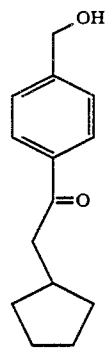

The product of Example E (2.2 g, 0.01 mole) was dissolved in THF (50 mls) and cooled under argon to 0° C. Lithium tri-t-butoxyaluminum hydride (2.7 g) was added portionwise over ½ hour at 0° C. and stirred for 2 hours at 0° C. The mixture was allowed to stir a total of 4 hours until thin layer chromatography indicated the reaction was complete. The mixture was then poured into 0.5N KHSO₄ and extracted with ethyl acetate. After drying the organic layer over Na₂SO₄, the solvent was removed to give 2.2 g of title compound (97% yield) as an oil.

EXAMPLE G

Preparation of 1-[4-(Chloromethyl)Phenyl]-2-Cyclopentylethanone

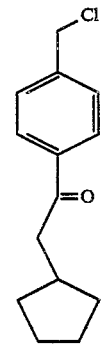

The product of Example F (450 mg, 0.002 mole) was dissolved in 5 mls of benzene and 250 mg of thionyl chloride was added. The mixture was refluxed for one hour. After cooling, the solution was poured into dilute K₂CO₃ and extracted with ethyl acetate. The organic phase was dried over Na₂SO₄, stripped and chromatographed on silica gel using 5% ethyl acetate/hexane as the eluent to give 275 mg of the title compound as an oil (56% yield).

EXAMPLE H

Preparation of Cyclohexaneacetyl Chloride

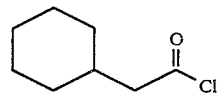

Following the procedure of Example A, 37 g (0.262moles) of cyclohexane acetic acid was converted to the title compound.

EXAMPLE I

Preparation of N-Methoxy-N-Methyl Cyclohexaneacetamide

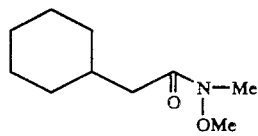

Following the procedure of Example B, 16 g (0.1mole) of the product of Example H was converted to the title compound. Purification of the title compound via chromatography on silica gel using 20% ethyl acetate/hexane as the eluent gave 9 g (50% yield) of the title compound.

EXAMPLE J

Preparation of 2-Cyclohexyl-1-[4-(2-Dioxolanyl)Phenyl]Ethanone

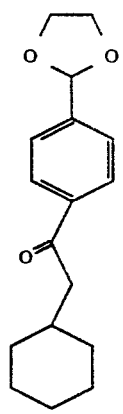

Following the procedure of Example D, 11 g (0.048mole) of p bromobenzaldehyde ethylene acetal and 8.9 g of the product of Example I were combined to give after chromatography on silica gel using 15% ethyl acetate/hexane 11 g of the title compound (84% yield).

EXAMPLE K

Preparation of 4-(2-Cyclohexyl-1-Oxoethylbenzenecarboxaldehyde

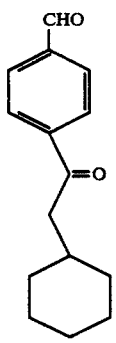

Following the procedure of Example E, 3 g (0.01moles) of the product of Example J was hydrolyzed in 50 mls of THF containing 7 mls of 1N HCl to give 2.4 g of the title compound (85% yield).

EXAMPLE L

Preparation of 2-Cyclopentyl-1-[4-(Hydroxymethyl)Phenyl]Ethanone

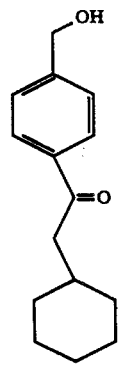

Following the procedure of Example F, the product of Example K 2.5 g (0.011mole) was reduced in 35 mls of THF containing 3.5 g of lithium tri-tert-butoxy aluminum hydride to give 2.25 g of the title compound (90% yield).

EXAMPLE M

Preparation of 1-[4-(Chloromethyl)Phenyl]-2-Cyclohexylethanone

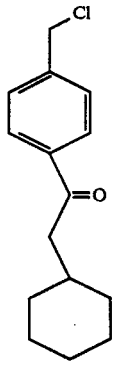

The product of Example L (2.25 g, 0.0097 moles) was added to 10 mls of thionyl chloride and refluxed for one hour. Thionyl chloride was removed via rotary evaporation and the residue was dissolved in ethyl acetate and washed with saturated NaHCO$_3$. The organic layer was dried over MgSO$_4$. After solvent removal the residue was chromatographed on silica gel using 5% ethyl acetate/hexane to give 1.8 g of the titled compound (74% yield).

EXAMPLE N

Preparation of 2-Cyclohexyl-1-[4(2-Dioxolanyl)Phenyl]-4-Penten-1-One

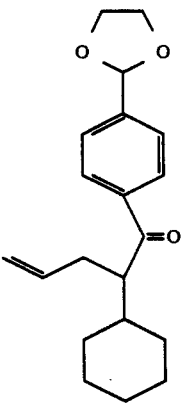

The product of Example J (1.6 g, 0.006 mole) was dissolved in 30 mls of dry DMF at room temperature under a nitrogen atmosphere and potassium t-butoxide (1.4 g) was added. After stirring for 5 minutes, 1 g of allyl iodide was added and the reaction was warmed to +50° C. for 1 hour. Another half equivalent of allyl iodide was added and the stirring was continued for 2 hours at +50° C. After cooling to room temperature the mixture was poured into 50 mls of 0.5N KHSO$_4$ and extracted with ethyl acetate. After drying the organic layer over Na$_2$SO$_4$, the solvent was removed and the residue was chromatographed on silica gel using 10% ethyl acetate/hexane to give 1 g of the title compound (54% yield).

EXAMPLE O

Preparation of 4-(2-Cyclohexyl-1-Oxo-4-Pentenyl)Benzenecarboxaldehyde

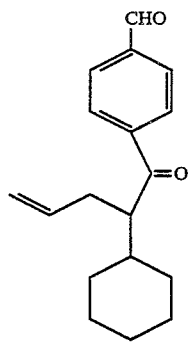

Following the procedure of Example E, 460 mg (0.0014 moles) of the product of Example N and 3 mls of 11N HCl gave the title compound 282 mg (75% yield).

EXAMPLE P

Preparation of 2Cyclohexyl-1-[4-Hydroxymethyl)Phenyl]-4-Penten-1-One

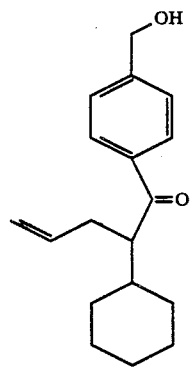

Following the procedure Example F, reaction of 280 mg (0.001 mole) of the product of Example O with 315 mg of lithium tri-t- butoxyaluminum hydride gave 250mg of the title compound (92% yield).

EXAMPLE Q

Preparation of 1-[4-(Chloromethyl)Phenyl]-2-Cyclohexyl-4-Penten-1-One

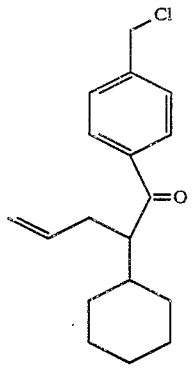

Following the procedure of Example M, 210 mg (0.00077 mole) of the product of Example P was refluxed in 3 mls thionyl chloride. The crude product was chromatographed on silica gel using 5% ethyl acetate/hexane to give 85 mg of the title compound (40% yield).

EXAMPLE R

Preparation of Methyl α-Cyclopentyl-1-Hydroxycyclohexaneacetate

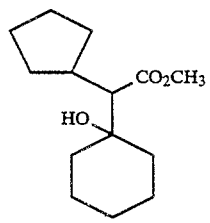

Diisopropylamine (12.7 g, 0.125) was dissolved in 150 mls of dry THF and cooled to −70° C. under $N_2$. n-Bulb (80 ml of 1.6M solution in hexane, 0.125 moles) was added and the solution stirred for 5 minutes at −70° C. Methyl cyclopentaneacetate (17 g, 0.125 mole) in 50 mls of THF was added at −70° C. over 15 minutes and the reaction was stirred at −70° C. for 15 more minutes. A solution of cyclohexanone (11.3 g, 0.115 moles) in THF (50ml) was then added at −70° C. over ½ hour and stirred in the cold for 1 hour. The reaction was warmed to room temperature over 1 hour and quenched with 5 mls of 1N HCl. The solvent was removed on the rotary evaporator and ethyl acetate added. The solution was then washed with saturated $NaHCO_3$ and the layers were separated. The organic layer was dried over $Na_2SO_4$. The drying agent was filtered and the filtrate stripped to give a residue which was chromatographed on silica gel using 7% ethyl acetate/hexane to give 27.8 g (92% yield) of the title compound.

EXAMPLE S

Preparation of Methyl
α-Cyclopentyl-1-Cyclohexen-1-Acetate

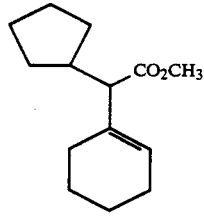

The product of Example R (16.25 g, 0.068 mole) was dissolved in pyridine (100 mls) containing 3 g of 4-dimethylaminopyridine at 25° C. Trifluoromethane sulfonic anhydride (20.0 g, 0.068 moles) was added dropwise under $N_2$ over 10 minutes. The temperature was increased to +50° C. for 15 minutes. After cooling the mixture to room temperature and stirring for 15 minutes, the reaction mixture was poured into 600 mls of 2N HCL and extracted with 1:1 ethyl acetate/ether. The organic phase was washed with brine and dried over $Na_2SO_4$. The filtration of the drying agent and removal of solvent gave 16 g of the title compound (99% yield).

EXAMPLE T

Preparation of Methyl α-Cyclopentyl Cyclohexaneacetate

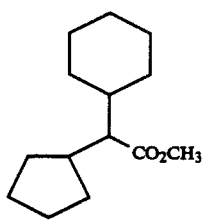

The product of Example S (15 g, 0.067 moles) was hydrogenated in methanol (150 mls) using W-2 RaNi (3 g) as catalyst at 5 psi and +25° C. for 20 hours until 97% of the theoretical uptake of hydrogen had been achieved. The reaction mixture was filtered and the filtrate concentrated. Distillation of the residue gave 14.5 g (96% yield) of the title compound (b.p. 85°–88° C. at 0.1 mmHg)

$C_{14}H_{24}O_2$: Calc: C, 74.95; H, 10.78. Found: C, 75.08; H, 11.20.

EXAMPLE U

Preparation of α-Cyclopentyl Cyclohexane Acetic Acid

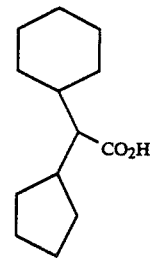

The product of Example T (5 g, 0.022 mole) was dissolved in 40 mls of DMF and 5 equivalents of LiI was added. The reaction mixture was then refluxed for 24 hours under $N_2$. The reaction was cooled, diluted with 25 mls of 0.5N $KHSO_4$ and extracted with ethyl acetate. After drying the organic layer over $Na_2SO_4$, the solvent was removed. Chromatography over silica gel using ethyl acetate/hexane/HOAc (5:95:1) gave 4 g of the title compound (87% yield).

$C_{13}H_{22}O_2$: Calc: C, 74.23; H, 10.54. Found: C, 73.78; H, 10.69.

EXAMPLE V

Preparation of α-Cyclopentyl-N-Methoxy-N-Methylcyclohexaneacetamide

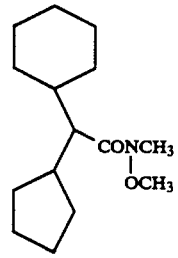

The product of Example U (3.25 g, 0.015 mole) was dissolved in 25 mls of thionyl chloride and then refluxed for 3 hours. The excess solvent was removed by distillation and the resulting residue was used in the next step.

O,N-dimethylhydroxylamine hydrochloride (4.5 g) was dissolved in 75 mls of dichloroethane containing 7.8 g of triethylamine under a nitrogen atmosphere. This solution was stirred for ½ hour and then the crude acid chloride prepared above was added at room temperature. After warming to 50° C., the reaction was stirred for 30 minutes. The solvent was removed after cooling and the residue was dissolved in ethyl acetate and washed with 0.5N $KHSO_4$. The organic layer was dried over $Na_2SO_4$. The drying agent was filtered and the filtrate concentrated on the rotary evaporator. The residue was chromatographed on silica gel using 10% ethyl acetate/hexane to give 3.3 g of the title compound (84% yield).

$C_{15}H_{27}O_2N$: Calc: C, 71.10; H, 10.74; N, 5.52 Found: C, 71.11; H, 10.39; N, 5.53

EXAMPLE W

Preparation of
2-Cyclohexyl-2-Cyclopentyl-1-[4-(2-Dioxolanyl)-Phenyl]Ethanone

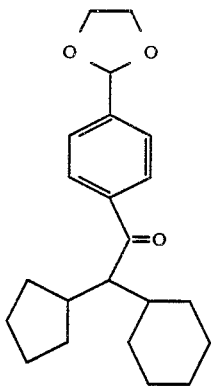

The product of Example C (3 g, 0.013 mole) was treated with tert-butyl lithium (19 mls of 1.6M/hexane) according to the procedure described in Example D. Then 3.2 g (0.013 moles) of the product of Example V was added to the reaction mixture. The mixture was then worked up according to the procedure described in Example D. Chromatography of the crude product on silica gel using 5% ethylacetate/hexane gave 730mg of a 1:1 mixture of the title compound and starting amide.

EXAMPLE X

Preparation of
4-(2-Cyclohexyl-2-Cyclopentyl-1-Oxoethylbenzenecarboxaldehyde

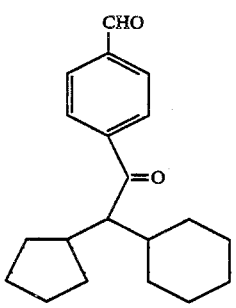

The crude material of Example W (730 mg) was treated with 5 mls of 1N HCL in 25 mls of THF and refluxed for 1 hour. The solvent was removed and the residue was extracted with ethyl acetate and the organic layer washed with brine. After drying and filtering, the solvent was removed and the residue was chromatographed twice on silica gel using 10% and then 5% ethyl acetate/hexane to give 175 mg of the title compound.

EXAMPLE Y

Preparation of
2-Cyclohexyl-2-Cyclopentyl-2-[4-(hydroxymethyl)-Phenyl]Ethanone

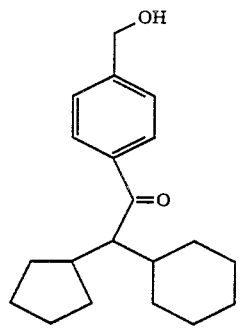

Following the procedure of Example F, 175 mg (0.00058 moles) of the product of Example X was converted to the title compound using lithium tri-t-butoxy aluminum hydride (175 mg) in THF. The product was chromatographed on silica gel using 25% ethyl acetate/hexane to give 140 mg of the title compound (79% yield).

EXAMPLE Z

Preparation of
1-[4-(Chloromethyl)Phenyl]-2-Cyclohexyl-2-CyclopentylEthanone

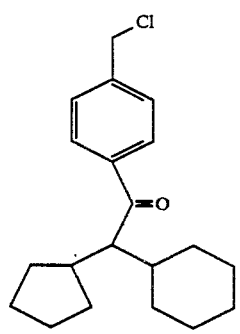

Following the procedure of Example M, 140 mg (0.46 mm) of the product of Example Y was converted to the chloride using 2 mls of SOCl₂. After chromatography of the crude product, 90 mg (61% yield) of the title compound was obtained.

FINAL PRODUCTS

EXAMPLE 1

Preparation of 2-Cyclopentyl-1-[4-(5H-Imidazo[4,5-c]Pyridin-5-yl-Methyl)Phenyl]Ethanone

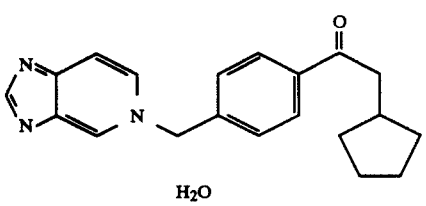

H₂O

The product of Example G (270 mg, 0.0011 moles) was dissolved in 5 mls of dimethylacetamide containing 135 mg (0.0011 moles) of 1H-imidazo[4,5-c]pyridine and stirred under nitrogen at 80° C. for 24 hours and at 115° C. for an additional 6 hours. The reaction appeared to be complete by TLC. After cooling, the solvent was removed by vacuum distillation. Chromatography of the crude product (twice) on silica gel using CH₃OH/CH₂Cl₂/NH₄OH (5/95/1) as the eluent gave 200 mg (57%) of the title compound as a monohydrate m.p.=153°-156° C.

$C_{20}H_{21}N_3O \cdot H_2O$: Calc: C, 71.19; H, 6.87; N, 12.45. Found: C, 71.06; H, 6.91; N, 12.45.

EXAMPLE 2

Preparation of 2 Cyclohexyl-1-[4-(5H-Imidazo[4,5-c]Pyridin 5-yl-Methyl)Phenyl]Ethanone

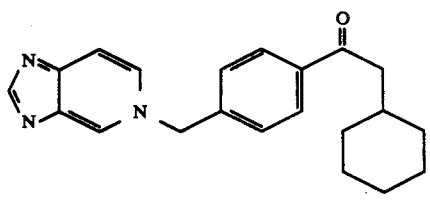

+0.5 H₂O

Following the procedure of Example 1, 1.8 g (0.0072 moles) of the product of Example M was added to 855 mg (0.0075 m) of 1H-imidazo]4,5-c]pyridine in 20 mls of dimethylacetamide and heated to 80° overnight. After chromatography with CH₂Cl₂/Ch₃OH/NH₄OH (95:4.5:1.5), 650 mgs of the title compound was obtained as a hemihydrate.

$C_{21}H_{23}N_3O \cdot \frac{1}{2}H_2O$ M.W. 342.40. Calc: C, 73.65; H, 7.06; N, 12.26. Found: C, 73.16; H, 7.02; N, 11.80.

EXAMPLE 3

Preparation of 2-Cyclohexyl-1-[4-(5H-Imidazo[4,5-c]Pyridin-5-yl-Methyl)Phenyl]-4-Penten-1-One

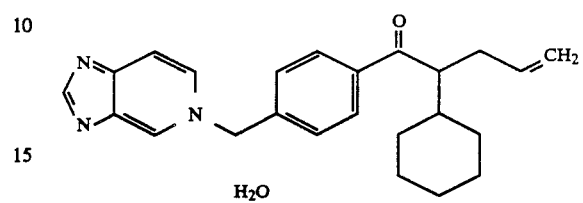

H₂O

Following the procedure of Example 1, 85mg (0.00029 moles) of the product of Example Q was reacted with 35mgs of 1H-imidazo[4,5-c]pyridine. The crude product was chromatographed on silica gel using MeOH/CH2Cl2/ NH4OH (5/94/1) as eluent to give 65 mg (60% yield) of the title compound.

$C_{24}H_{27}N_3O \cdot H_2O$. M.W.=391.48. Calc: C, 73.62; H, 7.46; N, 10.73. Found: C, 73.45; H, 7.62; N, 10.66.

EXAMPLE 4

Preparation of 2-Cyclohexyl-2-Cyclopentyl-1-[4-(5H Imidazol[4,5-c]Pyridin-5-yl-Methyl)Phenyl]Ethanone

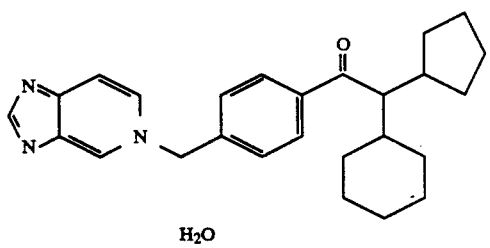

H₂O

Following the procedure of Example 1 90 mg (0.29 mmole) of the product of Example Z was reacted with 34 mg of imidazopyridine. The crude product was chromatographed on silica gel using MeOH/CH₂Cl₂/NH₄OH (5/94/1) as eluent to give 60 mg (49%) of the title compound as the monohydrate.

$C_{26}H_{31}N_3O \cdot H_2O$: M.W.=491.53. Calc: C, 74.43; H, 7.93; N, 10.01. Found: C, 74.31; H, 7.81; N, 9.94.

EXAMPLE 5

Preparation of 2-Cyclohexyl-1-[4-(5H-Imidazo[4,5-c]Pyridin-yl-Methyl)Methoxy Phenyl]Ethanone

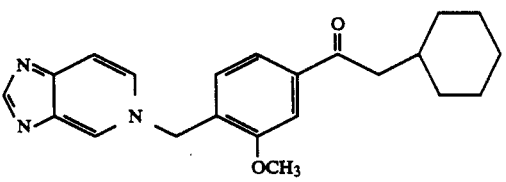

Following the procedure described in Example 1 1-[(4-chloromethyl,3-methoxy)phenyl]-2-cyclohexylethanone is converted to the title compound.

EXAMPLE 6

PAF-induced platelet aggregation and secretion: Washed, [$^3$H]serotonin-labeled rabbit platelets were prepared as previously described in COX, C. P , J. LINDEN and S. I. SAID: VIP elevates platelet cyclic AMP (cAMP) levels and inhibits in vitro platelet activation induced by platelet activating factor (PAF). *Peptides* 5:25–28, 1984, and maintained in an atmosphere of 5% $CO_2$ at 37° C. until used in the bioassay. Aliquots of platelets ($2.5 \times 10^8$/ml) were incubated with either an antagonist of PAF or the appropriate vehicle for 60 sec prior to the addition of PAF (0.2 nM to 0.2 µM). Aggregation was continuously monitored on a strip-chart recorder and recorded as the height of the tracing at 60 sec after the addition of PAF. Secretion of [$^3$H] serotonin was measured in a sample of the platelet suspension removed at 60 sec after the addition of PAF. The percent inhibition of aggregation and secretion was calculated by comparing antagonist-treated platelets with the appropriate vehicle-treated control platelets. Each combination of antagonist and PAF was repeated using different platelet preparations. $IC_{50}$ values were determined by inspection of the dose-response curves.

EXAMPLE 7

Inhibition of $^3$H-PAF Binding to Human Platelet Membrane Receptors

Receptor Preparation: Ten units of in-dated human packed platelets, each containing 45-65 ml platelet rich-plasma, were purchased from a commercial blood bank. Disposable plasticware was used throughout for receptor preparation. The units were pooled and a 1 ml aliquot was removed for determination of platelet concentration, using a Coulter Counter. The remaining platelet rich plasma was dispensed into 50 ml conical tubes and centrifuged at room temperature for 15 minutes at 3000 RPM (2300×g). Plasma was decanted and the platelets were resuspended in 35 ml of buffer (10 mM Trizma 7.0, 2 mM EDTA (dipotassium salt), and 150 mM KCl) and transferred to fresh tubes, which were centrifuged again as above. The platelets were washed 3 times, avoiding contaminating erythrocytes at the bottom of the pellets. Pellets were consolidated at each step, and by the last wash with EDTA/KCl buffer, most of the erythrocytes were in 1 tube. The pellets were resuspended in buffer containing 10 mM Trizma 7.0 with 10 mM $CaCl_2$. Following centrifugation, the buffer was decanted and the pellets were resuspended in the $CaCl_2$ buffer, avoiding erythrocyte contamination by recovering less than 100% of the platelet pellets. The resuspended platelets were dispensed in 8-10 ml aliquots into Corex tubes and disrupted by three cycles of freezing (dry ice/ethanol) and thawing (24° C.). The tubes were centrifuged at 40,000×g for 20 minutes at 4° C. Supernatants were decanted and each pellet was resuspended in 5–7 ml 10 mM Trizma 7.0. All resuspended pellets were pooled and aliquots of about 1200 µl were dispensed into 1.5 ml microfuge tubes and frozen at −70° C. Protein content was determined by a fluorescamine protein assay.

Assay Methods: Receptor Characterization—Each receptor preparation was evaluated to determine the number of receptor populations, the number of PAF receptor equivalents/mg protein and the dissociation constant ($K_D$) for PAF binding. This required 2-3 experiments in which the protein concentration was held constant and the $^3$H-PAF ligand concentration was varied from approximately 0.10–2.5 nM and the data was analyzed by Scatchard methodology. Total incubation volume was 250 µl for these procedures and incubations were conducted at 24° C. for 30 minutes. For further experimentation, total incubation volumes are 500 µl. Protein and ligand concentrations were adjusted to give 0.075 nM receptor equivalents in the presence of 0.75 nM $^3$H-PAF. Each receptor preparation was then used to determine the dose—response displacement relationship of unlabeled PAF and the PAF antagonist, triazolam. As long as the $K_D$ value and $IC_{50}$ values for PAF and triazolam were consistent with similar data collected from past receptor preparations used in the assay, the new receptor preparation was used for evaluating compounds.

Assay Methods: Routine Assay of Compounds—The compounds were weighed precisely and solubilized in quantities of DMSO such that a 5 µl aliquot in the incubate would deliver the desired compound concentration. Compounds tested for the first time in this assay were evaluated at a concentration of 50 µM in the incubation medium. All compounds were generally solubilized in DMSO for about 2 hours prior to assay. Triazolam was always included in each screening assay as a compound inhibition control. A standard concentration of 50 µM inhibited $^3$H-PAF binding by approximately 50%. Nonspecific binding control solution was made by drying to completion about 26.2 µl unlabeled PAF under a stream of argon. PAF was resolubilized in 1000 µl DMSO. When delivered in a 5 µl aliquot, the final concentration of 1 µM PAF in the incubate exceeded by 1000-fold the concentration of $^3$H-PAF.

All buffers containing proteins were made at room temperature on the day of assay. Assay buffer was prepared by adding 125 mg human albumin to 25 ml of stock buffer (10 mM Trizma 7.4 with 20 mM $CaCl_2$). Rinse buffer was made by adding 20 grams bovine serum albumin to 1000 ml stock buffer. About 80 ml of rinse buffer was decanted into a small pyrex dish and used to soak 65 Whatman GF/C 2.5 cm glass filters. The remaining rinse buffer was poured into a repipet and placed into an ice bath along with the filters.

Ligand for assay was prepared by adding about 10 µl of stock $^3$H-PAF (DuPont NEN, NET-668) to 14 ml of assay buffer. Since the amount of $^3$H-PAF in the final incubate was to be 0.75 nM, the actual amount of stock $^3$H-PAF to be used had to be determined for each lot of material based upon its specific activity.

Membrane receptors for assay were prepared by thawing the appropriate number of tubes at room temperature and adding membranes to 10 mM Trizma 7.0 containing 10 mM $CaCl_2$. A total volume of 14 ml was made. The actual amount of membranes needed was determined by the requirement to have 0.075 nM PAF receptor equivalents per assay tube. All materials were kept in motion by rocking on a rocker plate.

First, 5 µl of compound or DMSO was added to each 12×75 mm polypropylene tube, followed by the addition of 95 µl assay buffer. Next, 200 µl $^3$H-PAF was added to each tube and 3 aliquots of $^3$H-PAF taken at different times during the dispensing were placed in scintillation vials. The reaction was initiated by the addition of 200 µl of membranes. All tubes were very briefly vortexed and placed in a 24° C. water bath for about 30 minutes. During this time, Whatman GF/C filters were placed on the filter racks of 5 Millipore vacuum manifolds. The incubations were terminated by first adding 4 ml ice-cold rinse buffer to each incubation tube and then decanting them over the filters under vacuum. Tubes and filters were rinsed twice more. Each filter was placed into a 20 ml scintillation vial to which 20 ml Aquasol (DuPont NEN, NDF 952) was added. All vials were given 2 hours in the dark for photo and chemiluminence to dissipate prior to liquid scintillation counting.

In summary, each incubation tube contained 500 μl total volume of incubate. This consisted of 5 μl drug with DMSO or only DMSO, 95 μl assay buffer, 200 μl $^3$H-PAF (0.75 nM final concentration) and 200 microliters membrane receptors (0.075 nM final concentration). 60 tubes per assay were run and each dose was performed in triplicate. Controls in every assay consisted of 2 diluent (DMSO) "0" controls (2 triplicate determinations placed at different positions within the 60 tube assay), 1 nonspecific binding control, and 1 triazolam drug control. The 16 remaining doses were used to test 16 different compounds at the screening dose of 50 μM, or to run dose-response determinations for a compound. In general, dose-response curves were composed of 4 compound doses designed to inhibit $^3$-PAF binding by 15–85%, with at least 1 dose on each side of the 50% point.

Routine Assay Calculations: Triplicate DPM determinations (corrected for background) within a single compound dose were averaged while all 6 determinations of total binding ("0" dose, DMSO only) were averaged. The amount for nonspecific binding (1. μM PAF) was subtracted from all the dose averages, giving an amount of specific binding in all cases. The percent displacement of $^3$H-PAF or inhibition of binding was calculated by the formula STBo-SBc/STBo×100, where STBo=specific binding of "0" dose controls and SBc=specific binding in the presence of compound. If a compound tested at the initial screening dose of 50 μM inhibited binding by 45% or more, the compound was considered active and was tested in a dose-response manner to determine an IC$_{50}$ value. Compounds inhibiting PAF binding by less than 45% at a 50 μM concentration were considered inactive and no further testing was done.

IC$_{50}$ values were determined on active compounds in subsequent tests. Three or more compound doses must inhibit $^3$H-PAF binding between 15–85%. Using a computer program, % displacement data was transformed (logit) and a least squares linear regression was performed on the data meeting the 15–85% requirement to determine IC$_{50}$ values from data points derived from the same assay.

| Compound | Rabbit Platelet Secretion IC$_{50}$ (nM) | Rabbit Platelet Aggregation IC$_{50}$ (nM) | Human Platelet Receptor IC$_{50}$ (nM) |
|---|---|---|---|
| 2-cyclopentyl-1-[4-(5H-imidazo[4,5-c]pyridin-5-yl-methyl)phenyl]ethanone | 379 | 2587 | 8.41 |
| 2-cyclohexyl-1-[4-(5H-imidazo[4,5-c]pyridin-5-yl-methyl)phenyl]ethanone | 131 | 948 | 4.44 |
| 2-cyclohexyl-1-[4-(5H-imidazo[4,5-c]pyridin-5-yl-methyl)phenyl]-4-penten-1-one | 105 | 633 | 2.22 |
| 2-cyclohexyl-2-cyclopentyl-1-[4-(5H-imidazo[4,5-c]pyridin- | 89 | 279 | 1.46 |

| Compound | Rabbit Platelet Secretion IC$_{50}$ (nM) | Rabbit Platelet Aggregation IC$_{50}$ (nM) | Human Platelet Receptor IC$_{50}$ (nM) |
|---|---|---|---|
| 5-yl-methyl)phenyl ethanone | | | |

What is claimed is:
1. A compound of the formula

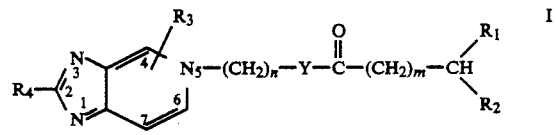

and isomers thereof;
or a pharmaceutically acceptable acid addition salt thereof: wherein
R$_1$ and R$_2$ are each independently selected from hydrogen; straight or branched chain alkyl of 1 to 15 carbon atoms; cycloalkyl of 3 to 8 carbon atoms; substituted cycloalkyl which can be substituted once or more by alkyl of 1 to 6 carbon atoms; phenyl; phenyl which can be substituted once or more by alkyl of 1 to 6 carbon atoms or halogen; straight or branched alkenyl having 3 to 15 carbon atoms. y is phenyl or phenyl substituted once or more by alkyl of 1 to 6 carbon atoms; alkoxy wherein the alkyl is 1 to 6 carbon atoms; and halogen selected from the group consisting of bromo, fluoro or chloro.
m is an integer from 0 to 5.
n is an integer from 1 to 5.
R$_3$ is a group substituted at one or more of the 4, 6 or 7 positions of the pyridine ring said groups being independently selected from hydrogen, alkyl of 1 to 6 carbon atoms; halogen wherein the halogen is selected from bromo, fluoro, or chloro; or alkoxy wherein the alkyl is 1 to 6 carbon atoms.
R$_4$ is hydrogen or alkyl of 1 to 4 carbon atoms.
2. A compound according to claim 1 having the formula

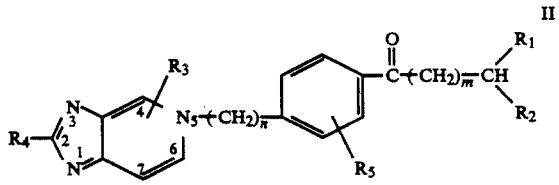

and isomers thereof;
or a pharmaceutically acceptable acid addition salt thereof: wherein
R$_1$ and R$_2$ are each independently selected from hydrogen; straight or branched chain alkyl of 1 to 15 carbon atoms; cycloalkyl having 3 to 8 carbon atoms; substituted cycloalkyl wherein the substituent is alkyl of 1 to 6 carbon atoms; straight or branched alkenyl having 3 to 15 carbon atoms;
m is an integer from 0 to 5.
n is an integer from 1 to 5.
R$_3$ is hydrogen or alkyl of 1 to 6 carbon atoms.
R$_4$ is hydrogen or alkyl of 1 to 4 carbon atoms.

$R_5$ is selected from hydrogen; alkyl of 1 to 6 carbon atoms; alkoxy wherein the alkyl is 1 to 6 carbon atoms; and halogen selected from the group consisting of bromo, fluoro or chloro.

3. A compound according to claim 2 which is 2-cyclopentyl-1-[4-(5H-imidazo[4,5-c]pyridin-5-yl-methyl)phenyl]ethanone.

4. A compound according to claim 2 which is 2-cyclohexyl-2-cyclopentyl-1-[4-(5H-imidazo [4,5-c]pyridin-5-yl-methyl)phenyl]ethanone.

5. A compound according to claim 2 which is 2-cyclohexyl-1-[4-(5H-imidazo[4,5-c]pyridin-5-yl-methyl)phenyl]-4-penten-1-one.

6. A compound according to claim 2 which is 2-cyclohexyl-1-[4-(5H-imidazo[4,5-c]pyridin-5-yl-methyl)phenyl]ethanone.

7. A pharmaceutical composition useful for treating diseases or disorders mediated by platelet-activating factor comprising at least one compound according to claim 1, together with one or more non-toxic pharmaceutically acceptable carriers.

8. A pharmaceutical composition according to claim 7 wherein said compound is 2-cyclopentyl-1-[4-(5H-imidazo[4,5-c]pyridin-5-yl-methyl)phenyl]ethanone.

9. A pharmaceutical composition according to claim 7 wherein said compound is 2-cyclohexyl-2-cyclopentyl-1-[4-(5H-imidazo[4,5-c]pyridin-5-yl-methyl)phenyl]ethanone.

10. A pharmaceutical composition according to claim 7 wherein said compound is 2-cyclohexyl-1-[4-(5H-imidazo[4,5-c]pyridin-5-yl-methyl)phenyl]-4-penten-1-one.

11. A pharmaceutical composition according to claim 7 wherein said compound is 2-cyclohexyl-1-[4-(5H-imidazo[4,5-c]pyridin-5-yl-methyl)phenyl]ethanone.

12. A method for treating diseases or disorders mediated by platelet-activating factor comprising administering a therapeutically effective dose of at least one compound of claim 1 to a mammal in need of such treatment.

13. A method according to claim 12 wherein said compound is 2-cyclopentyl-1-[4-(5H-imidaz [4,5-c]pyridin-5-yl-methyl)phenyl]ethanone.

14. A method according to claim 12 wherein said compound is 2-cyclohexyl-2-cyclopentyl-1-[4-(5H-imidazo[4,5-c]pyridin-5-yl-methyl)phenyl]ethanone.

15. A method according to claim 12 wherein said compound is 2-cyclohexyl-1-[4-(5H-imidazo[4,5-c]pyridin-5-yl-methyl)phenyl]-4-penten-1-one.

16. A method according to claim 12 wherein said compound is 2-cyclohexyl-1-[4-(5H-imidazo[4,5-c]pyridin-5-yl-methyl)phenyl]ethanone.

* * * * *

UNITED STATES PATENT AND TRADEMARK OFFICE
CERTIFICATE OF CORRECTION

PATENT NO. : 4,988,707

DATED : Jan. 29, 1990

INVENTOR(S) : Stealey, et. al.

It is certified that error appears in the above-identified patent and that said Letters Patent is hereby corrected as shown below:

Column 2, line 27, reading "straight o branched" should read -- straight or branched --.

Column 3, line 9, reading "All of these sakts nat be" should read -- All of these salts may be --.

Column 3, line 61, reading "with reagents such a t butyl lithium." should read -- with reagents such as t butyl lithium.--.

Column 10, line 29, reading "4.2 g, 0.024moles) of" should read -- 4.2g, 0.024 moles of --.

Column 15, line 40, reading "2Cyclohexyl" should read -- 2 Cyclohexyl --.

Column 21, line 63, reading "1H-imidazo]4,5c]" should read -- 1H-imidazo[4,5-c] --.

Signed and Sealed this

Twenty-ninth Day of December, 1992

*Attest:*

DOUGLAS B. COMER

*Attesting Officer*     *Acting Commissioner of Patents and Trademarks*